United States Patent [19]
Hunter et al.

[11] 3,954,788
[45] May 4, 1976

[54] 5-TRIFLUOROMETHYL-7-NITROBENZIMIDAZOLES

[75] Inventors: Don L. Hunter; Robert A. Smith, both of Anaheim, Calif.

[73] Assignee: United States Borax & Chemical Corporation, Los Angeles, Calif.

[22] Filed: June 24, 1974

[21] Appl. No.: 482,043

Related U.S. Application Data

[63] Continuation-in-part of Ser. No. 344,326, March 23, 1973, abandoned.

[52] U.S. Cl................................. 260/309.2; 71/92
[51] Int. Cl.² ............... C07D 235/08; C07D 235/24
[58] Field of Search ............................... 260/309.2

[56] References Cited
UNITED STATES PATENTS

| | | | |
|---|---|---|---|
| 3,325,271 | 6/1967 | Goldsmith et al. | 260/309.2 |
| 3,652,580 | 3/1972 | Janiak et al. | 260/309.2 |

*Primary Examiner*—Natalie Trousof
*Attorney, Agent, or Firm*—James R. Thornton

[57] ABSTRACT

Benzimidazoles of the formula

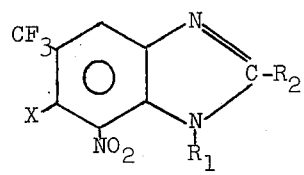

wherein $R_1$ and $R_2$ represent at least one alkyl group which may optionally be substituted and X is lower alkoxy or halo, $R_1$ may also be dialkyl amino and $R_2$ may be halo. The compounds are useful as intermediates for preparation of herbicides.

6 Claims, No Drawings

5-TRIFLUOROMETHYL-7-NITROBENZIMIDAZOLES

This is a continuation-in-part of our copending application Ser. No. 344,326 filed Mar. 23, 1973, now abandoned.

This invention relates to a novel class of substituted benzimidazoles and, more particularly, to a group of 5-trifluoromethyl-7-nitrobenzimidazoles which are useful as intermediates for preparation of herbicides. The novel benzimidazoles of this invention have the formula

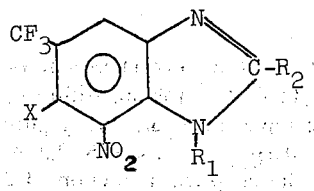

in which $R_1$ represents hydrogen, lower alkyl, halo-substituted lower alkyl, lower cycloalkyl, halo-substituted lower cycloalkyl, hydroxy-substituted lower alkyl, lower alkoxy-substituted lower alkyl or di-lower alkylamino; $R_2$ represents hydrogen, lower alkyl, lower cycloalkyl, hydroxy-substituted lower alkyl, lower alkoxy-substituted lower alkyl or halo; and X represents halo or lower alkoxy. For example, X can represent chloro or methoxy. Further, groups represented by $R_1 + R_2$ contain a total of at least one carbon atom, preferably about 2 to 6 carbon atoms.

Thus, the benzimidazoles must have a nitro group at the 7-position and a trifluoromethyl group at the 5-position of the molecule. Other possible substituents which are at the 6-position, represented by X in the above formula, include the halogens, such as bromo, chloro, iodo and fluoro, and lower alkoxy of 1 to about 6 carbon atoms such as methoxy, ethoxy, n-butoxy, and n-hexyloxy. Benzimidazoles having no substituent at the 1-position, can occur in two tautomeric forms and can be named, for example, 7(4)-nitro-5(6)-trifluoromethylbenzimidazoles. Both forms are meant to be included within the scope of the specification and claims.

$R_1$ and $R_2$ can each represent a lower alkyl or lower cycloalkyl substituent and may contain from 1 to about 6 carbon atoms, as for example, methyl, ethyl, n-propyl, isopropyl, sec-butyl, 3-pentyl, cyclopropyl, cyclobutyl, cyclohexyl, n-hexyl, and the like. The alkyl groups represented by $R_1$ can also have halo substituents, such as bromo, fluoro and chloro, lower alkoxy substituents, such as defined above, and hydroxy substituents. Examples of such groups include chloroethyl, bromoethyl, difluoroethyl, 3-bromopropyl, chlorocyclohexyl, 2-hydroxyethyl, methoxymethyl, 2,2-diethoxyethyl, 1-methyl-2-methoxyethyl, 2-methoxypropyl, di-chloromethyl, hydroxymethyl, chloromethyl and 3-hydroxypropyl. $R_1$ may also be a di-lower alkylamino group such as dimethylamino, diethylamino, di-propylamino and methylethylamino. $R_2$ can optionally have hydroxy or lower alkoxy substituents, as defined above, or may also represent halo, especially bromo or chloro. The 1- or 2-position of the benzimidazole molecule may be unsubstituted; however at least one, and preferably both, of the 1-and 2-positions are substituted. For example, $R_1$ can represent ethyl and $R_2$ can represent methyl.

Representative compounds, according to the present invention include:

7-nitro-2-methyl-6-ethoxy-5-trifluoromethylbenzimidazole
7-nitro-1-(2-bromoethyl)-6-chloro-5-trifluoromethylbenzimidazole
7-nitro-1-ethyl-2-methyl-6-fluoro-5-trifluoromethylbenzimidazole
7-nitro-1-sec-butyl-2-ethyl-6-chloro-5-trifluoromethylbenzimidazole
7-nitro-2-isopropyl-6-bromo-5-trifluoromethylbenzimidazole
7-nitro-2-n-hexyl-6-chloro-5-trifluoromethylbenzimidazole
7-nitro-1-ethyl-6-methoxy-2-methyl-5-trifluoromethylbenzimidazole
7-nitro-1-ethyl-6-chloro-2-methyl-5-trifluoromethylbenzimidazole
7-nitro-6-fluoro-1-ethyl-2-methyl-5-trifluoromethylbenzimidazole
7-nitro-6-chloro-1-cyclopropyl-2-methyl-5-trifluoromethylbenzimidazole
7-nitro-6-chloro-1-isopropyl-5-trifluoromethylbenzimidazole
7-nitro-6-bromo-2-hydroxymethyl-5-trifluoromethylbenzimidazole
7-nitro-2-chloro-1-isopropyl-6-methoxy-5-trifluoromethylbenzimidazole
7-nitro-2-(2-hydroxyethyl)-1-ethyl-6-chloro-5-trifluoromethylbenzimidazole
7-nitro-6-chloro-1-dimethylamino-2-methyl-5-trifluoromethylbenzimidazole
7-nitro-1-(1-methyl-2-methoxyethyl)-2-ethyl-6-bromo-5-trifluoromethylbenzimidazole
7-nitro-6-ethoxy-1-diethylamino-5-trifluoromethylbenzimidazole The compounds of this invention are generally crystalline solids, being soluble in organic solvents such as alcohol, acetone, the chlorinated hydrocarbons, benzene, etc. They are readily prepared by procedures known for the preparation of benzimidazoles such as the reaction of the corresponding substituted o-phenylenediamine with a carboxylic acid in the presence of a mineral acid according to the following equation

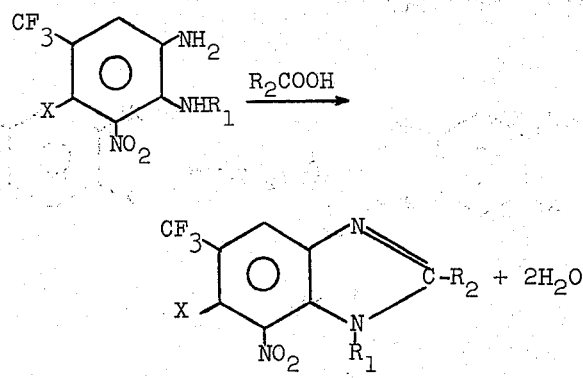

in which $R_1$, $R_2$ and X have the significance previously assigned.

Alternatively, a carboximidate may be employed in place of the carboxylic acid. Such carboximidates have the formula

in which R' is lower alkyl such as ethyl, and are generally used in their hydrochloride form. A suitable synthesis is illustrated as follows

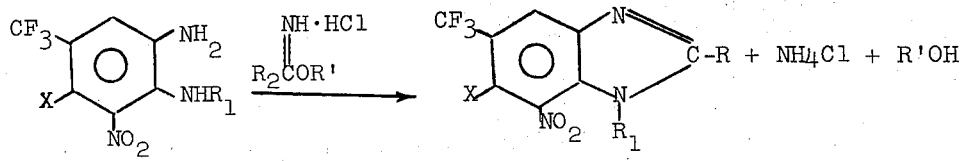

In many cases, it may be more convenient to prepare the benzimidazole free of a 7-substituent and then add the nitro group, such as by reaction with nitric acid or other suitable nitrating agents. A suitable synthesis is illustrated as follows

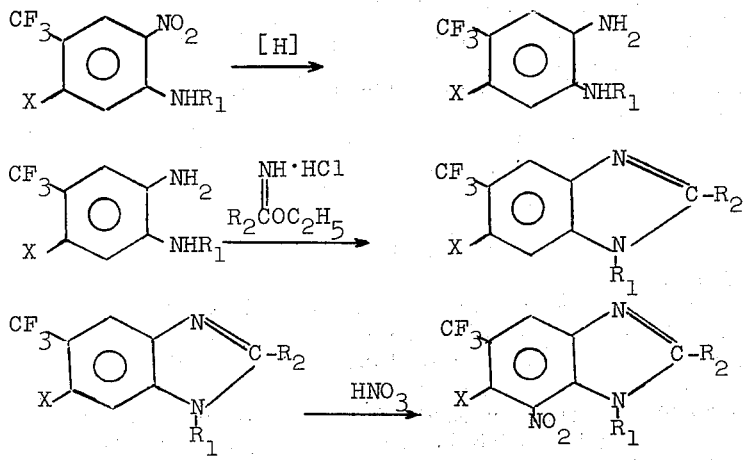

When $R_2$ is a halo group, the 7-nitrobenzimidazole compound can be prepared by halogenation of the corresponding benzimidazolone such as with phosphorus oxychloride or phosphorus oxybromide, as illustrated below, and then nitration of the resultant 2-halobenzimidazole.

See British Pat. No. 1,298,020 which describes preparation of 2,6-dinitro-3-halo-4-trifluoromethylanilines by reaction of a 2,4-dihalo-3,5-dinitrobenzotrifluoride with an amine, and U.S. Pat. No. 3,617,250 which shows preparation of 3-halo-6-nitro-4-trifluoromethylanilines by reaction of two moles of amine with one mole of 2,4-dihalo-5-nitrobenzotrifluoride. The halo group can be replaced by an alkoxy group by known procedures, if desired. See also U.S. Pat. No. 3,466,329 which shows the chemical reduction of 2,6-dinitro-4-trifluoromethylanilines employing sodium sulfide to produce the corresponding 6-nitro-4-trifluoromethyl-1,2-phenylenediamine.

The following examples illustrate the preparation of representative compounds of this invention and intermediates therefor.

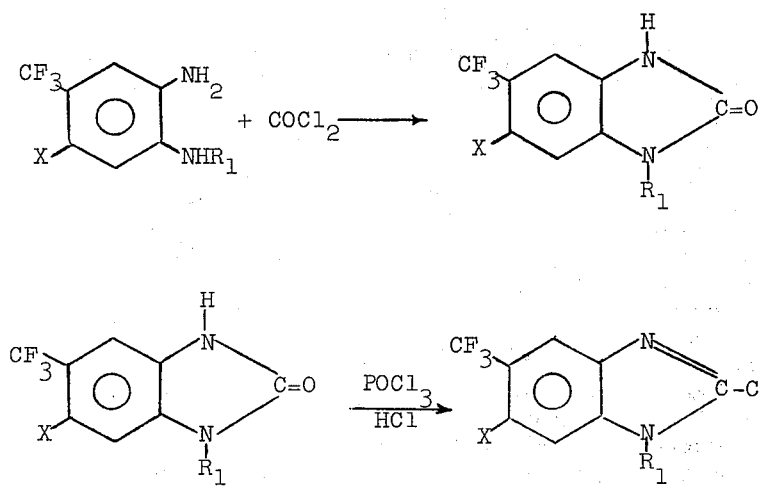

EXAMPLE I

N-Ethyl-3-chloro-6-nitro-4-trifluoromethylaniline

Aqueous ethylamine (70%; 29.7 g.; 0.46 mole) was added to a stirred solution of 60 g. (0.23 mole) of 2,4-dichloro-5-nitrobenzotrifluoride in 200 ml. of dimethoxyethane. The mixture was stirred for two hours while the exotherm subsided and then heated near reflux temperature overnight. The resulting mixture was evaporated to dryness at reduced pressure and the residue dissolved in chloroform. After washing twice with water, the chloroform solution was dried over sodium sulfate, filtered, and the solvent removed from the filtrate by distillation under reduced pressure. Crystallization of the residue from 95% ethanol gave 57.0 g. (87.1%) of N-ethyl-3-chloro-6-nitro-4-trifluoromethylaniline, m.p. 92.5° – 94.0°C.

EXAMPLE II

6-Chloro-1-ethyl-2-methyl-5-trifluoromethylbenzimidazole

A hydrogenation bottle was charged with 28.9 g. (0.108 mole) of N-ethyl-3-chloro-6-nitro-4-trifluoromethylaniline, 0.2 g. of platinum oxide catalyst, and 300 ml. of ethyl acetate. Shaking for 20.5 hours under 50 psi pressure resulted in the uptake of 3.94 mole equivalents (98.6%) of hydrogen. The catalyst was removed by filtration and the solvent evaporated from the filtrate. The resulting solid was dissolved in 200 ml. of ethanol and 14.62 g. (0.12 mole) of ethyl methylcarboximidate hydrochloride added. After 48 hours at room temperature, the solvent was removed and the residue dissolved in chloroform and filtered. Removal of the chloroform by distillation followed by recrystallization of the residue from hexane gave 20.3 g. (71.9%) of the product as yellow-red crystals, m.p. 118° – 119°C.

EXAMPLE III

6-Chloro-1-ethyl-2-methyl-7-nitro-5-trifluoromethylbenzimidazole

To a solution of 11.0 g. (0.04 mole) of 6-chloro-1-ethyl-2-methyl-5-trifluoromethylbenzimidazole dissolved in 110 ml. of concentrated sulfuric acid was added 11 ml. of 90% fuming nitric acid while cooling with an ice bath. The addition required three hours and the resulting red-brown solution was stirred for 6 hours at 0°C. and then at room temperature for 2.5 days. After pouring onto ice, the product was precipitated by the addition of 350 ml. of concentrated ammonium hydroxide. The crude solid was isolated and dissolved in 300 ml. of chloroform. The chloroform solution was washed with water, dried over $Na_2SO_4$, filtered, and the filtrate evaporated. Crystallization of the residual solid from hexane-$CCl_4$ (3:1) gave 9.0 g. (70%) of reddish solid, m.p. 114° – 116°C., whose nuclear magnetic resonance pattern confirmed it to be the desired product.

EXAMPLE IV

N-Ethyl-3-methoxy-6-nitro-4-trifluoromethylaniline

A solution of 14.0 g. (0.052 mole) of N-ethyl-3-chloro-6-nitro-4-trifluoromethylaniline and 16.98 g. (0.057 mole) of 18.23% methanolic sodium methoxide in 25 ml. of anhydrous methanol was sealed in a glass tube and heated at 119°C. for 88 hours. Removal of the solvent by distillation left a yellow solid residue which was triturated with hot chloroform. Filtration and evaporation of chloroform from the filtrate gave a crude solid residue. Crystallization of the residue from ethanol gave 12.4 g. of yellow crystalline product, m.p. 140.5° – 141.5°C. shown by its NMR spectrum to be the desired methoxyaniline.

EXAMPLE V

1-Ethyl-6-methoxy-2-methyl-5-trifluoromethylbenzimidazole

A solution of 24.4 g. (0.09 mole) of N-ethyl-3-methoxy-6-nitro-4-trifluoromethylaniline in 200 ml. of ethyl acetate, plus 100 ml. of ethanol, was hydrogenated in the presence of 0.2 g. of platinum oxide at room temperature. The theoretical amount of hydrogen was absorbed in 19 hours of shaking at 60 psi. The catalyst was removed by filtration and the solvent evaporated at reduced pressure. The solid residue was dissolved in 200 ml. of absolute ethanol and 12.58 g. (0.10 mole) of ethyl methylcarboximidate hydrochloride added. The mixture was stirred overnight at room temperature and the solvent removed at reduced pressure. Trituration of the brown residue with 200 ml. of chloroform, filtration, and evaporation of solvent from the filtrate left the crude residual product. Crystallization from hexane-$CCl_4$ (3:1) gave 18.1 g. (76%) of brown, shiny needles. Recrystallization from hexane gave the pure product, m.p. 127° – 129.5°C. whose structure was confirmed by an NMR spectrum.

EXAMPLE VI

1-Ethyl-6-methoxy-2-methyl-7-nitro-5-trifluoromethylbenzimidazole

1-Ethyl-6-methoxy-2-methyl-5-trifluoromethylbenzimidazole (11.0 g.; 0.04 mole) was added in portions over three hours to a cooled mixture of 110 ml. of concentrated sulfuric acid and 11 ml. of 90% white fuming nitric acid. The resulting brown solution was held at 0°C. for 6 hours and then at 25°C. for three days. Addition to ice water followed by neutralization with 350 ml. of concentrated aqueous ammonia gave a brown, oily precipitate. The product was extracted thrice with 100 ml. of chloroform, the extracts washed with water, dried over $Na_2SO_4$, filtered, and the chloroform removed by distillation. The residue was crystallized from 3:1 hexane-$CCl_4$ to give 5.5 g. (42.7%) of yellow solid. Recrystallization from hexane gave the desired product, m.p. 84° – 85.5°C.

EXAMPLE VII

7-Nitro-2,6-dichloro-1-ethyl-5-trifluoromethylbenzimidazole

6-Chloro-1-ethyl-5-trifluoromethylbenzimidazolone was prepared by reaction of $N^1$-ethyl-4-trifluoromethyl-5-chloro-1,2-phenylenediamine with phosgene. The resultant benzimidazolone was chlorinated with $POCl_3$—HCl to give the corresponding 2-chlorobenzimidazole which was then nitrated with $HNO_3$—$H_2SO_4$ to give the 7-nitro derivative, m.p. 117° – 118.5°C.

EXAMPLE VIII

7-Nitro-6-chloro-1-(dimethylamino)-2-methyl-5-trifluoromethylbenzimidazole

A solution of 5.2 g. of $N^2$-(dimethylamino)-4-chloro-3-nitro-5-trifluoromethyl-1,2-phenylenediamine (prepared by hydrogenation of the corresponding 3,5-dinitro-4-hydrazinobenzotrifluoride in the presence of palladium catalyst) and 7.5 g. of ethyl methylcarboximidate hydrochloride in 60 ml. of ethanol was refluxed for 26 hours. The resultant 7-nitrobenzimidazole was separated by fractionation on a silica gel column, m.p. 160° – 162°C.

EXAMPLE IX

7-Nitro-6-chloro-1-(2-hydroxyethyl)-5-trifluoromethylbenzimidazole

A mixture of 0.5 g. of 4-chloro-$N^2$-($\beta$-hydroxyethyl)-3-nitro-5-trifluoromethyl-1,2-phenylenediamine and 0.5 g. of formic acid was refluxed in 40 ml. of 4N hydrochloric acid for 24 hours. The resultant mixture was neutralized with ammonium hydroxide, extracted with chloroform, dried and then evaporated to dryness. The resultant nitro-benzimidazole melts at 147° – 150°C. after recrystallization from chloroform.

Other compounds representative of the present invention, which can be prepared according to the above-described procedures, include:

7-Nitro-6-chloro-1-n-propyl-5-trifluoromethylbenzimidazole, m.p. 93.5°–94.5°C.
7-Nitro-6-chloro-1-isopropyl-5-trifluoromethylbenzimidazole, m.p. 91.5°–92.5°C.
7-Nitro-6-chloro-1-cyclopropyl-2-methyl-5-trifluoromethylbenzimidazole, m.p. 144°–145°C.
7-Nitro-6-chloro-1-isopropyl-2-n-propyl-5-trifluoromethylbenzimidazole, m.p. 100°–101.5°C.
7-Nitro-6-chloro-1-isopropyl-2-methyl-5-trifluoromethylbenzimidazole, m.p. 132°–133.5°C.
7-Nitro-6-chloro-1-isopropyl-2-ethyl-5-trifluoromethylbenzimidazole, m.p. 116.5°–118.5°C.
7-Nitro-6-chloro-1-ethyl-2-isopropyl-5-trifluoromethylbenzimidazole, m.p. 92°–93°C.
7-Nitro-6-chloro-1-n-propyl-2-isopropyl-5-trifluoromethylbenzimidazole; oil.
7(4)-Nitro-6(5)-chloro-2-methyl-5(6)-trifluoromethylbenzimidazole, m.p. 211°–214°C.
7-Nitro-6-chloro-1,2-dimethyl-5-trifluoromethylbenzimidazole, m.p. 123°–127°C.
7-Nitro-1-n-butyl-2-methyl-6-chloro-5-trifluoromethylbenzimidazole, m.p. 93°–94.5°C.
7-Nitro-1-sec-butyl-2-methyl-6-chloro-5-trifluoromethylbenzimidazole, m.p. 95°–96°C.
7-Nitro-1-(3-pentyl)-2-methyl-6-chloro-5-trifluoromethylbenzimidazole; oil.
7-Nitro-6-chloro-2-sec-butyl-5-trifluoromethylbenzimidazole; oil.
7-Nitro-6-chloro-1-ethyl-2-hydroxymethyl-5-trifluoromethylbenzimidazole, m.p. 151°–153°C.
7-Nitro-6-methoxy-1-methyl-2-chloro-5-trifluoromethylbenzimidazole, m.p. 99°–101.5°C.
7-Nitro-6-methoxy-1-ethyl-2-chloro-5-trifluoromethylbenzimidazole, m.p. 88°–90°C.
7-Nitro-6-chloro-1-(1-methyl-2-methoxyethyl)-2-methyl-5-trifluoromethylbenzimidazole, m.p. 71°–72°C.
7-Nitro-6-chloro-1,2-diisopropyl-5-trifluoromethylbenzimidazole, m.p. 148°–153°C.
7-Nitro-2,6-dichloro-1-methyl-5-trifluoromethylbenzimidazole, m.p. 176°–177°C.
7-Nitro-2,6-dichloro-1-isopropyl-5-trifluoromethylbenzimidazole, m.p. 140°–143°C.
7-Nitro-6-methoxy-1-isopropyl-2-methyl-5-trifluoromethylbenzimidazole, m.p. 129°–133°C.
7-Nitro-6-chloro-1-(2-hydroxyethyl)-2-methyl-5-trifluoromethylbenzimidazole, m.p. 162°–163°C.

The compounds of the present invention are useful as intermediates for preparing herbicidal 7-amino-5-trifluoromethylbenzimidazoles. They are reduced to the corresponding 7-amino benzimidazole by reaction with hydrogen in the presence of a catalyst such as platinum oxide according to the following equation:

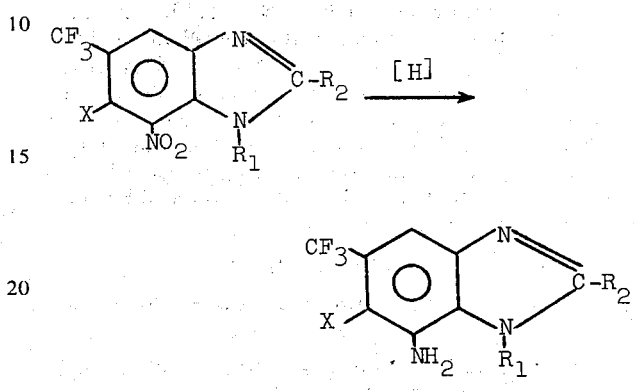

The following examples illustrate the conversion of the present compounds to the corresponding 7-amino benzimidazoles.

EXAMPLE X

7-Amino-1-ethyl-6-methoxy-2-methyl-5-trifluoromethylbenzimidazole

1-Ethyl-6-methoxy-2-methyl-7-nitro-5-trifluoromethylbenzimidazole (3.88 g.; 0.01 mole) in 50 ml. of ethyl acetate was hydrogenated in the presence of 0.1 g. of platinum oxide catalyst. Shaking for 20.5 hours at room temperature resulted in the uptake of 80% of the amount of hydrogen needed to reduce the nitro group. Filtration to remove the catalyst was followed by solvent removal and trituration with hot CCl$_4$. The hot CCl$_4$ solution was filtered and the solvent evaporated at reduced pressure leaving 3.3 g. (95%) of solid product. Two recrystallizations from CCl$_4$ gave the pure product, m.p. 171.5°–174.5°C.

EXAMPLE XI

7-Amino-6-chloro-1-ethyl-2-methyl-5-trifluoromethylbenzimidazole

About 5 g. (0.02 mole) of 6-chloro-1-ethyl-2-methyl-7-nitro-5-trifluoromethylbenzimidazole was hydrogenated in 100 ml. of methanol in the presence of 0.15 g. of platinum oxide. The theoretical amount of hydrogen was absorbed in four hours of shaking. After filtration and removal of the methanol, the crude product was crystallized from carbon tetrachloride to give 2.3 g. (51%) of reddish-brown solid, m.p. 176°–178°C. An NMR spectrum confirmed the structure as 7-amino-6-chloro-1-ethyl-2-methyl-5-trifluoromethylbenzimidazole.

The following examples illustrate the herbicidal activity of the 7-amino-5-trifluoromethylbenzimidazoles.

EXAMPLE XII

7-Amino-1-ethyl-2-methyl-6-chloro-5-trifluoromethylbenzimidazole was evaluated as a post-emergence treatment on a broad class of representative crops and weeds. The compound and its hydrochloride salt were tested according to the following procedure at a rate of 1 pound per acre.

Greenhouse flats were planted to the crops and weeds. After the plants had emerged and were about 1 inch in height, the flats were sprayed with an ethanol solution of the compound and a water solution of the salt at a rate of 1 pound per acre. The flats were kept in the greenhouse and watered when needed. Twenty-one days after treatment, the flats were examined and the plants rated for herbicidal activity on a 0 to 9 scale in which 0 = no effect, 5 = substantial injury with some kill, and 9 = complete kill. The results are shown in Table I.

TABLE I

| Plant | Activity Rating Compound | HCL Salt |
|---|---|---|
| Cotton | 5/3 | 9 |
| Corn | 0 | 1 |
| Soybeans | 7/2 | 9 |
| Wheat | 1 | 0 |
| Barley | 1 | 1 |
| Field Beans | 9 | 7/3 |
| Mustard | 9 | 8/4 |
| Foxtail | 9 | 8/3 |
| Coffeeweed | 9 | — |
| Velvetleaf | 9 | 9 |
| Millet | 9 | 9 |
| Peanuts | 5/3 | 2 |
| Pigweed | 9 | 9 |
| Jimsonweed | 7/3 | 8/4 |
| Teaweed (Prickly sida) | 6/4 | 8/4 |
| Watergrass | 8/4 | 7/3 |
| Morningglory | 9 | 9 |
| Sorghum | 5/3 | 1 |
| Rice | — | 1 |

In Table I, where there are two numbers, i.e. 7/3, the first is percent kill on a 5–9 scale and the second is a percent injury to the remaining plants on a 0–4 scale. Thus,

| | | | |
|---|---|---|---|
| 0 = | no effect | 5 = < | 25% kill |
| 1 = < | 10% injury | 6 = | 25–50% kill |
| 2 = | 10–40% injury | 7 = | 50–75% kill |
| 3 = | 40–70% injury | 8 = | 75–99% kill |
| 4 = > | 70% injury | 9 = | complete kill |

Reference is made to copending applications of Don L. Hunter, Robert A. Smith and Wayne S. Belles, Ser. No. 333,902 filed Feb. 20, 1973, now abandoned, and Ser. No. 476,012, filed June 3, 1974, which describe and claim the novel 7-amino-5-trifluoromethylbenzimidazoles and their use as herbicides.

Various changes and modifications of the invention can be made and, to the extent that such variations incorporate the spirit of this invention, they are intended to be included within the scope of the appended claims.

What is claimed is:

1. A compound of the formula

in which $R_1$ represents di-lower alkylamino; $R_2$ represents hydrogen or lower alkyl; and X represents halo or lower alkoxy.

2. A compound of the formula

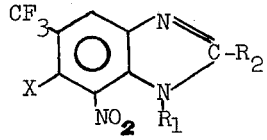

in which $R_1$ represents hydrogen, lower alkyl, halo-substituted lower alkyl, lower cycloalkyl, halo-substituted lower cycloalkyl, hydroxy-substituted lower alkyl, lower alkoxy-substituted lower alkyl or di-lower alkylamino; $R_2$ represents halo; X represents halo or lower alkoxy and in which $R_1 + R_2$ contains a total of at least one carbon atom.

3. A compound in accordance with claim 2 in which said X is chloro.

4. A compound in accordance with claim 2 in which said $R_2$ is chloro.

5. 7-Nitro-2,6-dichloro-1-ethyl-5-trifluoromethylbenzimidazole.

6. 7-Nitro-2,6-dichloro-1-isopropyl-5-trifluoromethylbenzimidazole.

* * * * *